(12) United States Patent
Pratt

(10) Patent No.: US 6,457,760 B1
(45) Date of Patent: Oct. 1, 2002

(54) HIGH SPEED INSERTION BAILER HAVING SNAP-IN SPIDER FOR VALVE ALIGNMENT

(76) Inventor: David W. Pratt, 13512 Feather Sound Cir. West, Apt. 1401, Clearwater, FL (US) 33762

( * ) Notice: Subject to any disclaimer, the term of this patent is extended or adjusted under 35 U.S.C. 154(b) by 2 days.

(21) Appl. No.: 09/595,612

(22) Filed: Jun. 16, 2000

Related U.S. Application Data

(63) Continuation-in-part of application No. 09/513,384, filed on Feb. 25, 2000, now Pat. No. 6,286,880, and a continuation-in-part of application No. 09/349,068, filed on Jul. 8, 1999, now Pat. No. 6,167,962, and a continuation-in-part of application No. 09/313,799, filed on May 18, 1999, now Pat. No. 6,135,523.

(51) Int. Cl.$^7$ .............................. F16K 1/32; F16K 3/00
(52) U.S. Cl. ................ 294/68.25; 73/864.63; 137/533.21; 251/333
(58) Field of Search .................. 294/68.22, 68.25; 73/864.63, 864.65, 864.66; 137/238, 244, 533.17, 533.19, 533.21, 904; 251/333, 334, 357, 358, 368, 85; 166/66, 162, 165, 66.6, 66.7, 99

(56) References Cited

U.S. PATENT DOCUMENTS

| | | | | |
|---|---|---|---|---|
| 485,092 | A | * 10/1892 | Davis ..................... | 294/68.25 |
| 742,451 | A | * 10/1903 | Ladley .................... | 294/68.25 |
| 760,570 | A | * 5/1904 | Schellhammer ......... | 294/68.25 |

(List continued on next page.)

FOREIGN PATENT DOCUMENTS

| | | | | |
|---|---|---|---|---|
| GB | 402933 | * 12/1933 | .............. | 294/68.25 |

Primary Examiner—Donald P. Walsh
Assistant Examiner—Paul T. Chin
(74) Attorney, Agent, or Firm—Ronald E. Smith; Smith & Hopen, PA

(57) ABSTRACT

A bailer that is substantially leak-free includes an improved valve housing at its lowermost end. A valve body in the form of a solid or hollow hemispherical ball is mounted at the lowermost end of a straight valve stem. The hemispherical valve body seats in a valve seat that matches the contour of the hemispherical exterior surface of the valve body. The valve body has a preselected specific gravity that enables it to float on the surface of the liquid fluid being sampled when the valve body is unrestricted. The valve stem is slideably received within and guided by a central aperture formed in a central hub of a spider member that spans the hollow interior of the valve housing. The spider is supported about its periphery by an annular shoulder formed in the interior sidewalls of the valve housing. The spider is inserted into the valve housing and pressed against the annular shoulder when the bailer is assembled. In this way, the spider is positively positioned and serves to limit the travel of the valve body away from the valve seat. The spider has four legs of equal length that radiate outwardly from the central hub. In a first embodiment, the legs collectively form a "+" when seen in plan view and an annular ring interconnects the outermost ends of the legs. A flange circumscribes the annular ring and engages the annular shoulder to provide positive positioning for the spider within the bailer. In a second embodiment, the legs are grouped into two pairs so that they collectively form an "X" shape when seen in plan view. The outermost ends of the legs in a pair are interconnected to one another by an arcuate segment to save materials. A flange is formed in each arcuate segment to engage the annular shoulder formed in the interior sidewall of the bailer, to provide positive positioning of the spider. In both embodiments, flutes are formed in peripheral walls that define the central aperture formed in the hub so that particulate matter does not become wedged between the valve stem and the peripheral walls. High speed insertion of the bailer into a body of liquid fluid is facilitated by weights secured to its leading and trailing ends and the weights at the leading end are covered by a shroud having an aerodynamically-shaped cap at its leading end. Alternatively, the shroud is eliminated and a weight housing having an aerodynamically shaped cap is detachably secured to the leading end of the bailer.

12 Claims, 6 Drawing Sheets

U.S. PATENT DOCUMENTS

| | | | | |
|---|---|---|---|---|
| 849,240 A | * | 4/1907 | Holman | 294/86.25 |
| 922,986 A | * | 5/1909 | Westway | 137/533.21 |
| 1,055,385 A | * | 3/1913 | Cahill | 294/68.25 |
| 1,210,487 A | * | 1/1917 | Kaul | 73/864.63 |
| 1,545,758 A | * | 7/1925 | Green et al. | 294/68.25 |
| 1,574,809 A | * | 3/1926 | Gilbreath | 294/68.22 |
| 2,025,296 A | * | 12/1935 | McIntyre | 137/533.17 |
| 2,223,936 A | * | 12/1940 | Hart | 294/68.25 |
| 2,333,711 A | * | 11/1943 | Dwiggins | 73/864.63 |
| 2,454,740 A | * | 11/1948 | Lehnhard, Jr. | 166/66 |
| 2,593,830 A | * | 4/1952 | Baker | 294/68.25 |
| 2,678,563 A | * | 5/1954 | Parrish | 73/864.65 |
| 2,951,538 A | * | 9/1960 | Martin | 166/162 |
| 3,455,904 A | * | 7/1969 | Hopkin | 73/864.63 |
| 3,796,238 A | * | 3/1974 | Roth | 294/68.25 |
| 3,815,422 A | * | 6/1974 | Niskin | 73/864.67 |
| 3,995,658 A | * | 12/1976 | Hager | 137/543 |
| 4,050,315 A | * | 9/1977 | Markfelt | 73/864.66 |
| 4,082,483 A | * | 4/1978 | Sprenger | 294/68.22 |
| 4,086,035 A | * | 4/1978 | Klaeger, Jr. et al. | 166/168 |
| 4,271,704 A | * | 6/1981 | Peters | 73/864.63 |
| 4,368,909 A | * | 1/1983 | Alexander, Jr. | 294/68.22 |
| 4,583,916 A | * | 4/1986 | Senghass et al. | 294/68.22 |
| 4,590,810 A | * | 5/1986 | Hunjin et al. | 73/864.63 |
| 5,454,275 A | * | 10/1995 | Kabis | 73/864.51 |
| 5,597,966 A | * | 1/1997 | Timmons | 73/864.63 |
| 5,878,813 A | * | 3/1999 | Ridgeway, Jr. | 166/162 |

\* cited by examiner

HIGH SPEED INSERTION BAILER HAVING SNAP-IN SPIDER FOR VALVE ALIGNMENT

CROSS-REFERENCE TO RELATED APPLICATIONS

This disclosure is a continuation-in-part of application Ser. No. 09/313,799, filed May 18, 1999, now U.S. Pat. No. 6,135,523, entitled "Bailer Having Leak-Inhibiting Seal." It is also a continuation-in-part of application Ser. No. 09/349,068, filed Jul. 8, 1999, now U.S. Pat. No. 6,167,962, entitled "Anti-Wobbling Bailer With High Speed Insertion." It is further a continuation-in-part of application Ser. No. 09/513,384, filed Feb. 25, 2000, now U.S. Pat. No. 6,286,880, entitled "Bailer Having Leak-Inhibiting Cushioned Seal." All of said related disclosures are by the present inventor and are hereby incorporated by reference and the first two disclosures are hereinafter referred to as the first and second incorporated disclosures, respectively.

BACKGROUND OF THE INVENTION

1. Field of the Invention

This invention relates, generally, to bailers. More particularly, it relates to a bailer that has a valve support and aligner assembly that is snapped into place at a lowermost end of the bailer. It also relates to a bailer having improved means for high speed insertion and improved means for preventing leakage.

2. Description of the Prior Art

Bailers are elongate cylindrical tubes that are lowered into container-held liquid fluids, natural bodies of water, and the like for the purpose of taking a sample of the liquid fluid so that laboratory tests can be performed thereon.

In the industry standard bailer, a free-floating ball valve at the lower end of the bailer unseats from its valve seat when the bailer is lowered into a liquid fluid, i.e., as liquid fluid flows upwardly into the hollow interior of the bailer. The ball valve sinks into seating relation to its valve seat when the liquid fluid stops flowing into the bailer. When properly seated, the ball valve should substantially prevent leakage of the liquid fluid from the hollow interior of the bailer.

In practice, however, the ball valve sometimes leaks profusely. The clothing of the person carrying the bailer to a vehicle that will transport the collected sample to a lab often gets wet as the liquid fluid within the bailer leaks past the ball valve. If the liquid fluid is an acid or other irritant, the leakage is more than a mere nuisance. Even if the liquid fluid is just water, the loss of sample is undesirable.

The seat for the ball valve is an annular step formed on an interior surface of a frusto-conical wall that provides a taper that interconnects the main body of the bailer with a reduced diameter downspout at the lowermost end thereof. A single grain of sand on the annular step can defeat proper seating of the ball valve. Sand particles and other particulate matter are commonly found in the liquid fluids that are collected by bailers in the field.

Moreover, leakage can occur due to manufacturing imperfections that cause the seating to be less than perfect, even when no particulate matter is present.

Since the ball valve is free-floating, it rises upwardly within the bailer as liquid fluid enters the bailer, there being no restriction that keeps the ball valve from such upward travel. After the upward flow of liquid fluid has ceased upon filling of the bailer, it takes several seconds or more for the ball valve to sink back to its valve seat at the lower end of the bailer. The ball valve sinks in water because its specific gravity is one or greater.

Thus, there are two time periods where the user of the bailer has to wait. First, the user must wait while the bailer sinks into the water or other liquid fluid and fills itself. Next, the user must wait for the free-floating ball valve to sink so that it returns to its seat. These waiting periods add up to a considerable amount of time when many samples are being taken. If the samples are being taken in hostile climates, such as polar regions, then the waiting periods are even more undesireable.

An improved bailer, more fully disclosed in the first incorporated disclosure, includes a valve seat in the form of an annular concavity formed in an interior surface of a lower part of the bailer. The lower part includes frusto-conical sidewalls. The annular concavity is configured to substantially match an exterior surface of a hemispherical valve body so that substantially no leakage of liquid fluid from the hollow interior of the bailer occurs when the hemispherical valve body is seated in the annular concavity.

The means for supporting and aligning the valve body in the first incorporated disclosure includes a spider positioned in the lower part of the bailer. The spider structure includes a plurality of legs of equal length that radiate from a hub at the center of the structure. The respective radially outermost ends of the legs are riveted or adhered to the inner sidewall of the bailer.

A central aperture is formed in the hub for slideably receiving a valve stem from which the valve body depends. In this way, the valve stem is coincident with the longitudinal axis of symmetry of the bailer, ensuring that the valve body is in proper alignment with its valve seat. The spider also limits upward travel, i.e., travel of the valve body away from the valve seat, so that the time required for the valve body to return to the valve seat is reduced.

The bailer of the first incorporated disclosure includes no means for positively locating the spider during assembly of the bailer. Instead, the assembler positions the spider in what appears to be an operable position, and secures the spider into said position by using an adhesive, rivets, or other fastening means.

The bailer of the first incorporated disclosure also includes no means for overcoming jamming problems caused by particulate entry into the central aperture formed in the hub of the spider. As a result, the valve stem may become stuck in its fully open or closed position, or any position therebetween, rendering the bailer inoperable, when sand or the like becomes wedged between a wall defining the periphery of the central aperture and the valve stem.

Nor is the spider member of the first incorporated disclosure designed to conserve materials or to speed the seating of the valve body after a sample has been taken.

The bailer of the second incorporated disclosure includes weighted members mounted to the leading and trailing ends of the bailer on an exterior surface thereof. These externally-mounted weights do not cause turbulence in the fluid being sampled as do internally-mounted weights. However, the weights are quite expensive and although they provide very fast insertion, they do not present an aerodynamic contour and thus their insertion speed is less than optimal.

It was not obvious to those of ordinary skill in this art how an improved means for positively positioning the spider and hence the valve body within the bailer could be provided, in view of the art considered as a whole at the time the present invention was made. Nor was it obvious how to overcome the jamming problem associated with particulate entry into the central aperture of the spider hub, or how to construct the spider in a way that would conserve materials. Moreover, it was not obvious how the cost of weighted bailers could be decreased and it was also not obvious how the bailer insertion speed and valve body seating speed could be increased.

SUMMARY OF THE INVENTION

The long-standing but heretofore unfulfilled need for an innovation that overcomes the limitations of the prior art is now met by a new, useful, and non-obvious invention. The present invention includes a substantially leak-free valve assembly for admitting liquid fluid into the hollow interior of a bailer as the bailer is lowered into a liquid fluid and for retaining liquid fluid within the hollow interior when the bailer is lifted from the liquid fluid. The novel assembly also provides externally-mounted inexpensive weights that are covered by an aerodynamically designed shroud to maximize insertion speed. In another embodiment, a weight housing, like the spider, can be snapped into position or otherwise attached to the leading end of the bailer.

The bailer is of the type that has an elongate cylindrical main body and a preferably separately-formed lower part or valve housing that is press fit or otherwise secured to the elongate cylindrical main body at its lowermost end. The valve housing has three parts that are integrally formed with one another. The first part is formed by cylindrical sidewalls and includes an annular shoulder formed on an external surface thereof that abuttingly engages the lowermost end of the elongate cylindrical main body of the bailer. The second part depends from the first and is formed by diameter-reducing frusto-conical sidewalls. The third part depends from the reduced diameter end of the second part and is formed by cylindrical sidewalls that form a downspout.

A valve support and alignment means in the form of a spider member spans a hollow interior of the first part of the valve housing. An annular shoulder formed on an interior surface of said first part provides a support means for the spider. The spider includes a central hub having a central aperture formed therein. The axis of symmetry of the central aperture is substantially coincident with a longitudinal axis of symmetry of the bailer. The central aperture slideably receives the valve stem from which a valve body depends and thus aligns it with the longitudinal axis of the bailer.

In a first embodiment, four legs of equal length radiate outwardly from the central hub and the respective outermost ends of the legs are equidistantly and circumferentially spaced apart from one another. Thus, the legs collectively form a "+" or cruciform configuration when viewed in plan view. An annular ring interconnects the outermost ends of the legs. In a first variation, the annular ring overlies the annular shoulder formed in the interior surface of the first part of the valve housing to positively position the spider. In a second, preferred variation, a thin, flange encircles the annular ring and the thin flange overlies the annular shoulder. A flexible and resilient annular ridge is formed in parallel, vertically spaced apart relation to the annular shoulder. The spacing is about the thickness (longitudinal extent) of the annular ring in the first variation and is about the thickness of the thin flange in the second variation. In this way, the spider is snap fit into place and no adhesives or. other fastening means are required to secure it into its operative position.

In a second, preferred embodiment, four legs of common length radiate outwardly from the hub, with the legs being grouped into two pairs of legs where each member of a first pair is substantially closer to the other member of the first pair than it is to either leg of the second pair. An arcuate segment interconnects the radially outermost ends of the legs of each pair, and the radially outermost ends of legs of different pairs are not interconnected, thereby saving materials.

In a first variation of the second embodiment, the arcuate segments overlie the annular shoulder formed in said interior surface. In a second, preferred variation a thin flange is formed along the extent of each arcuate segment, and said thin flange overlies said annular shoulder to provide the positive positioning means. The flexible and resilient annular ridge of the first embodiment is also provided in both variations of this second embodiment, for the same reason.

In both embodiments, the peripheral walls of the central aperture are fluted to overcome the problem caused by particulate matter accumulating in the central aperture of the spider hub.

Moreover, in both embodiments a hemispherical-in-configuration valve body having a hollow or solid construction is secured to a lowermost end of the valve stem, and that valve stem is slideably received within the central aperture formed in the spider hub as aforesaid. Accordingly, the hemispherical valve body rises and falls as liquid fluid flows into and out of the hollow interior of the bailer, respectively. The valve stem and the central aperture of the spider hub cooperate to maintain the hollow hemispherical valve body in substantial coincidence with the longitudinal axis of symmetry of the bailer as the hollow hemispherical valve body rises and falls. Moreover, the spider limits the distance the hemispherical valve body can travel away from to its valve seat.

The hemispherical valve body is made of plastic materials, preferably, having a specific gravity less than one so that said valve body floats on the surface of water if unrestricted. For liquid fluids other than fresh water, the specific gravity of the hemispherical valve body is adjusted as required so that it floats on the surface of the liquid fluid. The hemispherical valve body unseats from its valve seat more quickly than conventional ball valves when liquid fluid enters the bailer, because conventional ball valves have a specific gravity greater than one so that they can sink into their valve seat. The novel hemispherical valve body is returned to its seat not by sinking under its own weight but by the pressure of the water column above it. Being of hemispherical form, its trailing side is flat or concave, depending upon whether it is solid or hollow, respectively. Thus, the pressure of the water column returns it to its seat. A ball valve, on the other hand, has a spherical trailing side and the pressure applied by the water column is deflected and contributes little to the return of the valve body to its seat. Accordingly, the specific gravity of a spherical valve body must be one or greater so that it sinks into its valve seat under its own mass and not in reliance upon the pressure of the water column above it.

In both embodiments of the novel bailer, a valve seat in the form of an annular concavity is formed in an interior surface of the frusto-conical sidewalls. It is configured to substantially match an exterior surface of the hollow hemispherical valve body so that substantially no leakage of liquid fluid from the hollow interior of the bailer occurs when the hollow hemispherical valve body is perfectly seated against the annular concavity.

In one embodiment, the novel, inexpensive weight members at the leading end of the bailer are provided in the form of individual, central apertured bushings that are slidingly engaged on the downspout. The novel shroud is cylindrical in configuration and has a trailing end that slideably receives the cylindrical sidewalls of the first part of the valve housing. The novel shroud has a leading end adapted to be snap-fittingly engaged by an aerodynamic nose cone or cap that seals against the downspout to prevent liquid fluid entry into the shroud and that maximizes insertion of the bailer into the liquid fluid being sampled.

In another embodiment, the weight is provided by even less expensive materials, such as sand. The sand is poured into the space defined between the shroud and the valve housing and the novel cap is used to maintain the sand in said space. Alternatively, a measured amount of sand, such as two ounces, four ounces, etc., is placed into a small, elongate sand bag and that small, elongate sandbag is positioned into encircling relation with the downspout and housed by the shroud and the cap.

In yet another embodiment, use of the shroud is eliminated and a highly novel weight housing is provided. The novel weight housing can hold loose sand, a sand bag, or other inexpensive weight means. It is designed to snap onto the valve housing, preferably at its leading end to the downspout and at its trailing end to the frusto-conical walls of the valve housing. This eliminates the shroud and enables a customer order to be filled by snap fitting a weight housing of a known weight onto the valve housing in a negligible amount of time.

It is a primary object of this invention to provide an improved valve structure for bailers.

A more specific object is to advance the art of bailer manufacturing by providing a structure for positively positioning a spider and hence the valve means of a bailer.

Another object is to provide a spider structure that conserves materials.

Still another object is to provide a valve structure for bailers that reduces jamming of the valve structure by particulate matter.

Yet another object is to improve high speed insertion of bailers by making them less expensive and by enhancing their aerodynamic profile.

These and other important objects, features, and advantages of the invention will become apparent as this description proceeds.

The invention accordingly comprises the features of construction, combination of elements and arrangement of parts that will be exemplified in the construction hereinafter set forth, and the scope of the invention will be indicated in the claims.

BRIEF DESCRIPTION OF THE DRAWINGS

For a fuller understanding of the nature and objects of the invention, reference should be made to the following detailed description, taken in connection with the accompanying drawings, in which.

DETAILED DESCRIPTION OF THE PREFERRED EMBODIMENT

Figure 1A:
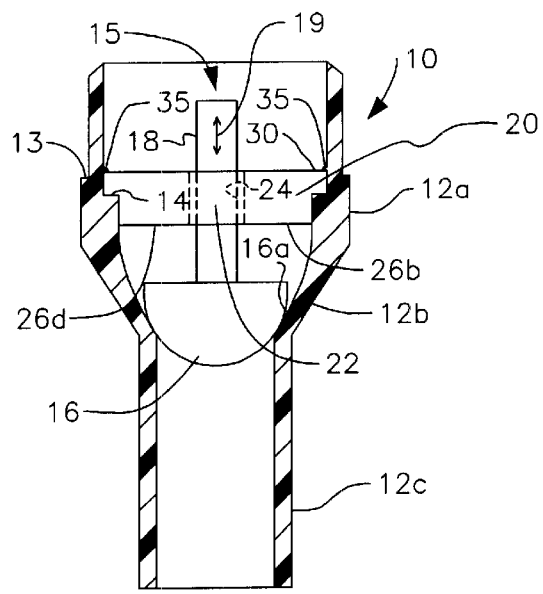
FIG. 1A is a longitudinal sectional view of a valve housing of a bailer, depicting a first embodiment of the novel spider in its operable position.

Referring now to FIG. 1, it will there be seen that the lower part or valve housing of an otherwise unillustrated bailer is denoted 10 as a whole. Said valve housing includes cylindrical sidewalls 12a, frusto-conical sidewalls 12b, and cylindrical sidewalls 12c having a diameter that is reduced relative to the diameter of sidewalls 12a. Said sidewalls 12c form the downspout of the bailer.

An annular shoulder 13 is formed in the exterior surface of sidewalls 12a. Shoulder 13 abuts the lowermost end of the unillustrated main body of the bailer when the bailer is assembled. In other words, sidewalls 12a are slideably received within the lower end of the main body of an assembled bailer. A bailer could also be made with valve housing 10 being formed integrally with the elongate cylindrical main body of the bailer, but such construction could increase the difficulty of final assembly.

An annular shoulder 14 is formed in the interior surface of cylindrical sidewalls 12a.

A valve means 15 includes a hemispherical valve body 16 and a straight valve stem 18. Valve body 16 may have a hollow or solid construction. If hollow, it presents a concave trailing surface to the column of liquid fluid above it. If solid, it presents a flat trailing surface to said column. Either way, the structure of the valve body harnesses the pressure of said column of liquid fluid as a force that drives the valve body back into its valve seat when liquid fluid stops flowing into the bailer. In the hollow embodiment, the hollow formed in the trailing side of valve body 16 is filled with liquid fluid and such extra liquid fluid enhances the sealing power of said valve body. In other words, the depth of the hollow increases the height and thus the pressure provided by the column of liquid fluid above said valve body.

Whether of solid or hollow construction, the novel valve body of this invention differs from all other known bailer valve bodies in that it has a specific gravity less than one so that it floats on the surface of water if unrestricted. If a different specific gravity is required to make it float in other liquid fluids, its specific gravity is adjusted as needed to provide said floatation feature. Thus, the hemispherical valve body unseats from its valve seat faster than a valve body of the prior art, because all heretofore known bailer valve bodies have a specific gravity of one or more to enable them to sink into sealing relation with their valve seat when sample collection is completed. The novel valve body returns to its seat faster than a conventional valve body because, unlike conventional valve bodies, it does not rely upon a sinking action to return it to its valve seat. Its flat or concave trailing end, depending upon whether or not it is solid or hollow, harnesses the pressure of the column of liquid fluid above it and this pressure returns the valve body to its seat faster than any sinking action. Moreover, since the novel spider restricts travel of the novel hemispherical valve body to a very short distance, such as an inch, the distance that the novel valve body must travel to return to its valve seat is substantially less. than the distance that must be traveled by a free-floating ball valve body.

An annular concavity 16a is formed in the interior surface of frusto-conical sidewalls 12b. Said annular cavity forms the seat for valve body 16, whether it is of solid or hollow construction.

Spider 20 supports and aligns valve means 15. Spider 20 includes a central hub 22 having a central aperture 24 formed therein. The center of aperture 24 is substantially coincident with the longitudinal axis of symmetry of the bailer.

Figure 2:
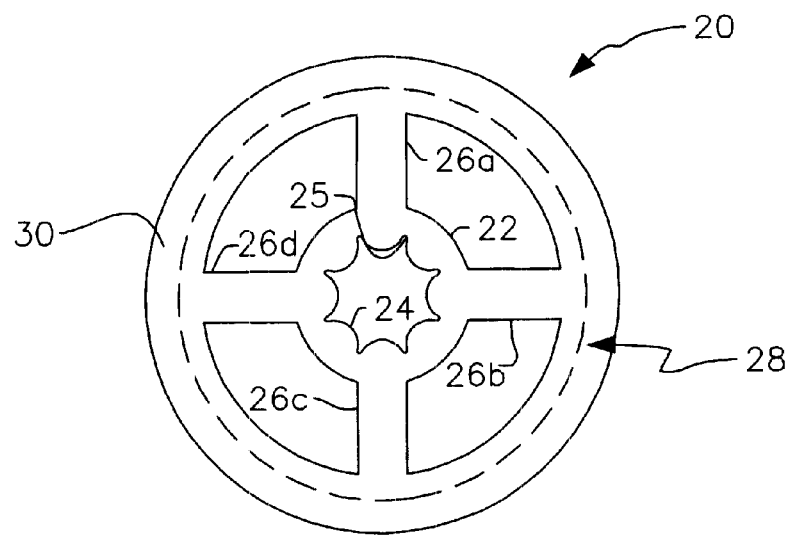
FIG. 2 is a top plan view of a first embodiment of the novel spider.
Figure 3:
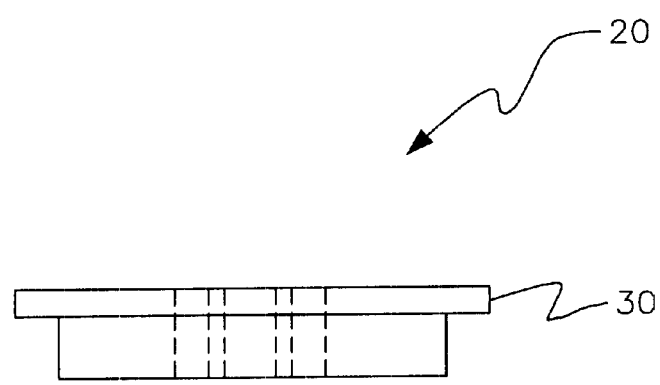
FIG. 3 is a side elevational view of said first embodiment.

In a first embodiment, depicted in FIGS. 2 and 3, legs 26a, 26b, 26c, and 26d of spider 20 share a common length and extend radially outwardly from central hub 22 in equidistantly and circumferentially spaced apart relation to one another. Accordingly, said legs collectively form a "+" or cruciform shape when seen in plan view.

An annular ring 28 interconnects the respective outermost ends of legs 26a–d. In a preferred embodiment, a thin flange 30 is formed integrally with annular ring 28 and extends! radially outwardly with respect thereto. As indicated in FIG. 1A, said thin flange 30 overlies annular shoulder 14 and is sandwiched between said shoulder and flexible and resilient annular ridge 35. It should therefore be understood that said thin flange 30, working in cooperation with shoulder 14, provides positive placement means for positioning spider 20 when the bailer is assembled.

Figure 1B:
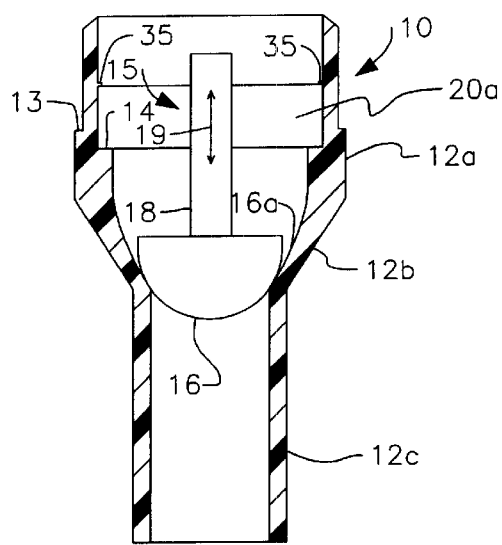
FIG. 1B is a longitudinal sectional view of the valve housing of a bailer, depicting a variation of the first embodiment of said novel spider in its operable position.

In a first variation of the first embodiment, depicted in FIG. 1B, flange 30 is obviated and annular ring 20a overlies annular shoulder 14 to provide a positive positioning means for spider 20. In this variation, annular ridge 35 is spaced further from shoulder 14 to accommodate the thickness of said annular ring 20a.

When spider 20 is properly installed, valve stem 18 is slideably inserted into central aperture 24. This positions the longitudinal axis of valve stem 18 in coincidence with the longitudinal axis of valve housing 10 and ensures proper seating of hemispherical valve body 16 with respect to annular concavity 16a formed in the interior surface of sidewalls 12c. More particularly, valve stem 18 slides up within central bore 24 as liquid fluid flows into the hollow interior of the bailer, and stem 18 slides downwardly when liquid is no longer flowing into the bailer, as indicated by double-headed directional arrow 19 in FIG. 1. Hemispherical valve body 16 thus rises and falls as well, guided by the sliding engagement between valve stem 18 and spider 20.

Figure 4:
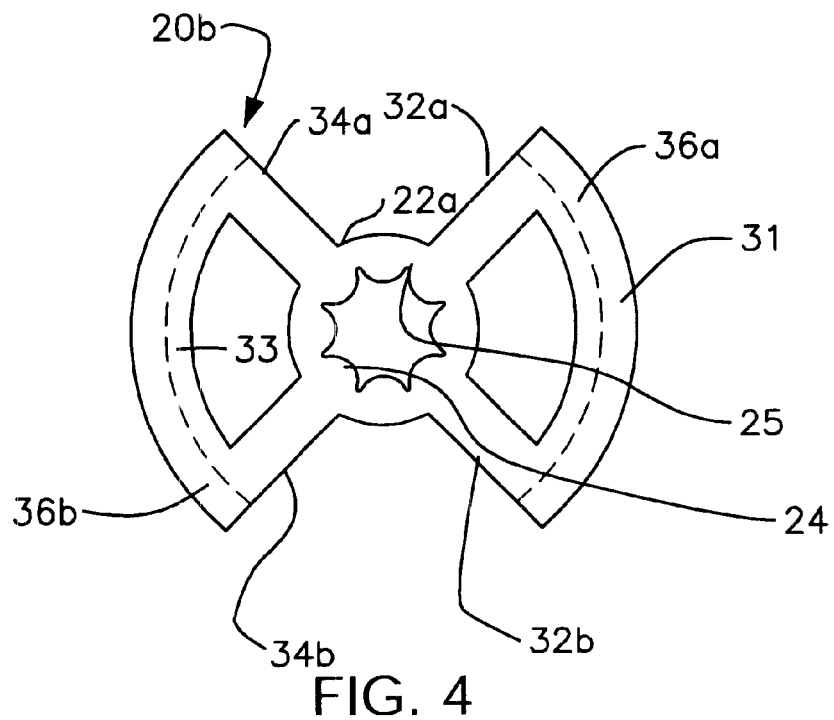
FIG. 4 is a top plan view of a second embodiment of the novel spider.
Figure 5:
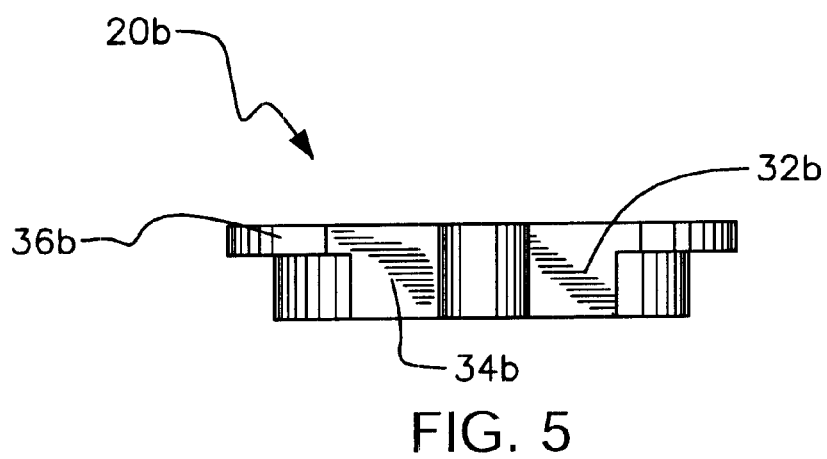
FIG. 5 is a side elevational view of said second embodiment.

Turning now to FIGS. 4 and 5, it will there be seen that in a second, preferred embodiment of spider 20, denoted 20b, a plurality of legs, denoted 32a, 32b and 34a, 34b, emanate radially from central hub 22a and have a common extent. Legs 32a, 32b form a first pair and legs 34a, 34b form a second pair. In this preferred embodiment, the legs of the first pair are closer to one another than they are to the legs of the second pair. In other words, they collectively form an "X" shape. An arcuate segment 31 and 33 interconnects the radially outermost ends of the legs of each pair, respectively. Thin flange 36a is formed integrally with arcuate segment 31 and thin flange 36b is formed integrally with arcuate segment 33. Said thin flanges 36a, 36b overlie annular shoulder 14 in the same way that thin flange 30 overlies said annular shoulder 14 in the first embodiment, there being less contact due to the truncate extent of said thin flanges 36a, 36b. Flexible and resilient annular ridge 35 overlies thin flanges 36a, 36b when spider 20b is fully seated. Said flexible and resilient annular ridge and annular shoulder 14 cooperate to provide snap fit engagement of said spider within valve housing 10. As in the first embodiment, a variation of this second embodiment eliminates thin flanges 36a, 36b and arcuate segments 31, 33 overlie annular shoulder 14. Flexible and resilient annular ridge 35 is then positioned in greater spaced apart relation to annular shoulder 14.

Spider 20b could have any number of radiating legs, and the invention is not limited to a spider having four legs as depicted. The "X" design of the spider conserves materials without sacrificing strength. Being supported by annular flange 14, it need not be riveted or otherwise attached to cylindrical sidewalls 12a. Moreover, annular shoulder 14 provides positive positioning of the spider, thereby easing assembly of the bailer and ensuring a high quality product.

Figure 6:
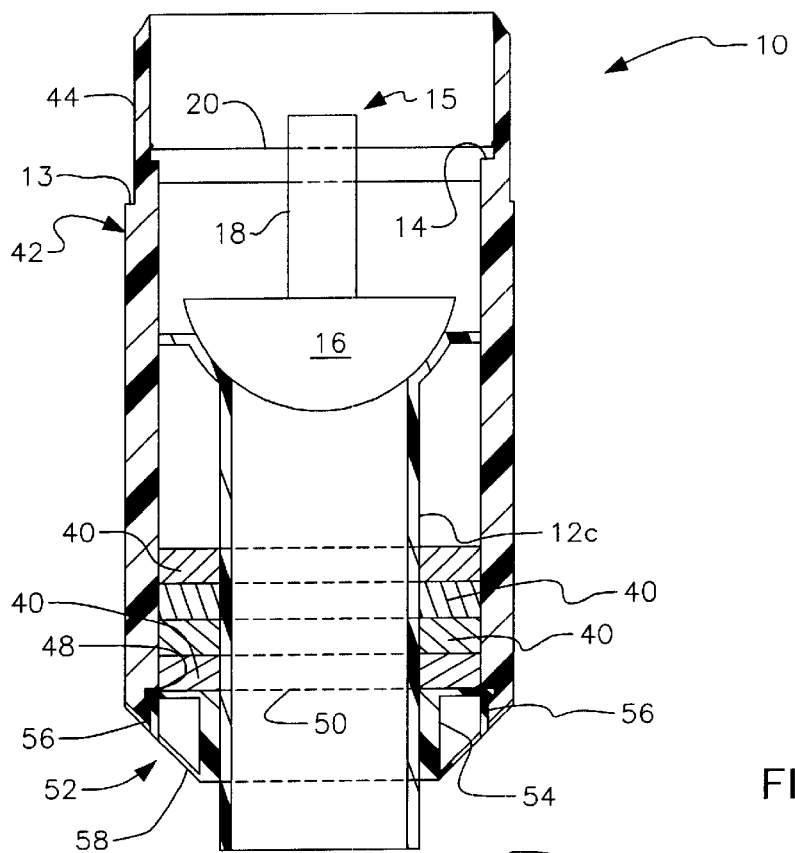
FIG. 6 is a longitudinal sectional view of a first embodiment of the novel shroud.
Figure 6A:
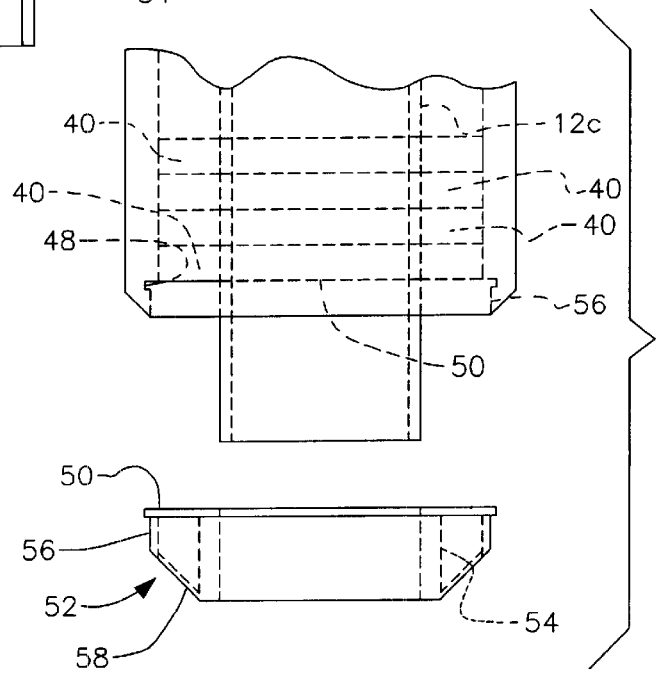
FIG. 6A is an exploded view of the lower part of FIG. 6.

FIG. 6 depicts weight members, collectively denoted 40, that are centrally apertured and slideably received upon downspout 12c. In a first embodiment, weight members 40 are covered by cylindrical shroud 42 having a trailing end 44 that is slidingly received within the cylindrical side walls of the unillustrated bailer. The leading end of the shroud is closed by aerodynamically contoured cap 52. Annular groove 48 is formed in an interior side wall of shroud 42 near its leading end and said groove 48 is snap-fittingly engaged by a base plate 50 that forms the base of cap 52. Cap 52 includes cylindrical inner sidewalls 54 that slidingly and sealingly engage the exterior cylindrical side walls of downspout 12c and cylindrical outer side walls 56 that abuttingly and sealingly engage the interior cylindrical side walls of shroud 42 in the region between annular groove 48 and the leading end of said shroud. A frusto-conical leading wall 58 extends from the leading end of cylindrical inner side walls 54 to the outer exterior surface of shroud 42 and is preferably integrally formed with cylindrical inner sidewalls 54 and outer cylindrical side walls 56, said inner and outer side walls being integrally formed with base plate 50 so that cap 52 is an integrated unit. Cap 52 prevents liquid fluid from entering into the hollow interior of shroud 42 and thus ensures that weight members 40 remain dry and thus do not corrode. Its aerodynamic profile also increases the speed of insertion of the bailer. Cap 52 need not be snap fittingly engaged to shroud 42; it may be releasably attached thereto by other means.

Figure 7:
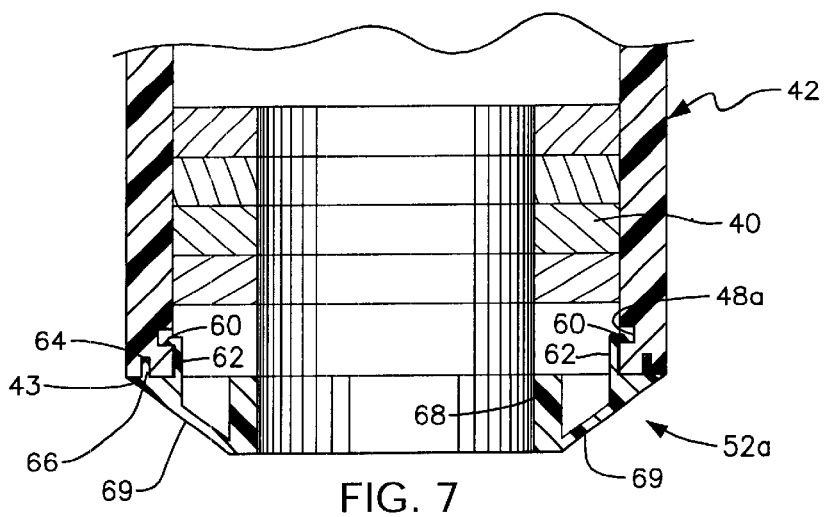
FIG. 7 is a longitudinal sectional view of a second embodiment of said shroud.
Figure 7A:
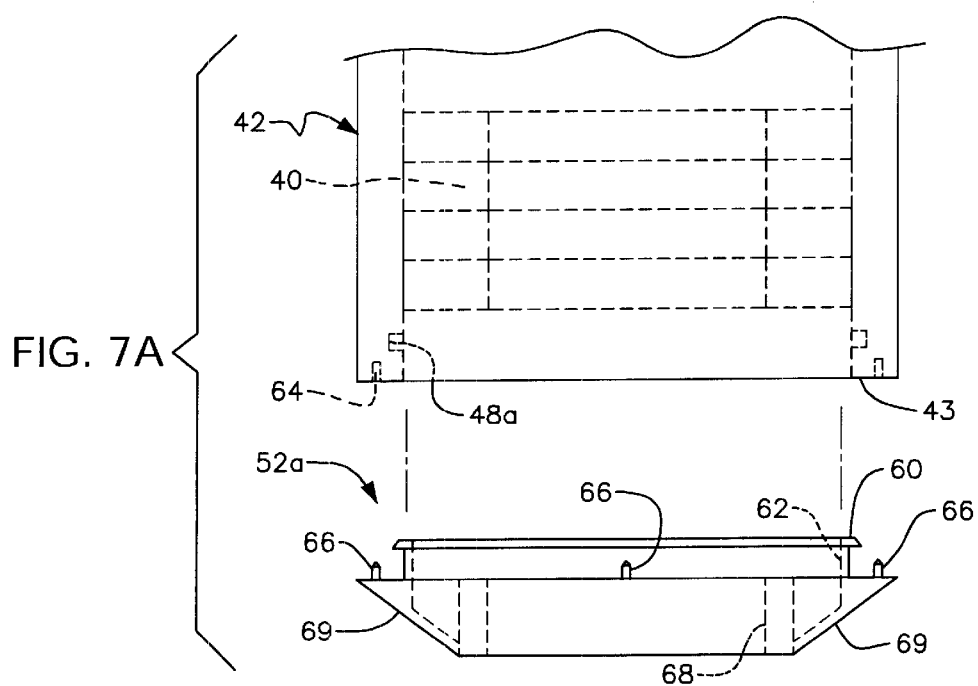
FIG. 7A is an exploded view of the lower part of FIG. 7.

FIGS. 7 and 7A depict another embodiment of cap 52; it is denoted 52a just to indicate that it has minor structural differences that distinguish it from cap 52. Annular groove 48a is formed in the interior cylindrical side wall of shroud 42 as in the embodiment of FIG. 6, and said annular groove is snap fittingly engaged by base plate 60 formed in the free end of flexible and resilient cylindrical side wall 62. A second annular groove 64 is formed in the leading peripheral edge 43 of shroud 42 and it snap fittingly receives annular ridge member 66 that extends in trailing relation from the main body of cap member 52a. Cylindrical walls 68 slidingly receive and sealingly engage downspout 12c. Materials are saved by making frusto-conical wall 69 quite thin. Cap 52a need not be snap fittingly engaged to shroud 42; it may be releasably attached thereto by other means.

Figure 8:
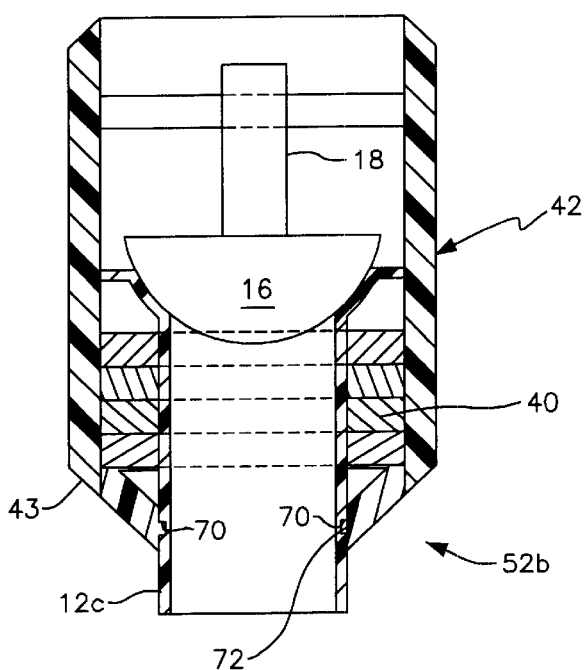
FIG. 8 is a longitudinal sectional view of a third embodiment of said shroud.
Figure 8A:
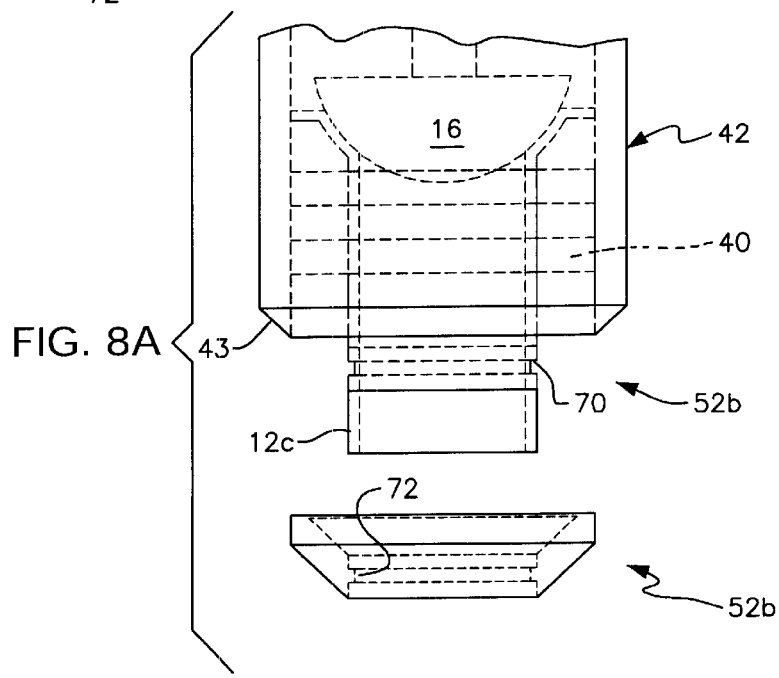
FIG. 8A is an exploded view of the lower part of FIG. 8.

Yet another embodiment of the shroud cap is depicted in FIGS. 8 and 8A; it is denoted 52b. An annular groove 70 is formed in downspout 12c. It snap fittingly receives annular ridge 72 formed in the leading end of cap 52b. The trailing end of said cap 52b is snap fittingly engaged to the leading peripheral edge 43 of shroud 42. Cap 52b need not be snap fittingly engaged to shroud 42; it may be releasably attached thereto by other means.

The embodiments of FIGS. 6–8 perform the same function in substantially the same way and achieve substantially the same result; they are provided just to indicate a few of the many alternative but equivalent designs that could be employed for cap 52. The important structural features of this particular embodiment include the cylindrical shape of the main body of the shroud means and the frusto-conical shape of the cap that provides a swept-back, aerodynamic profile that facilitates high speed insertion of the bailer into a body of liquid fluid. The trailing end of the cap is preferably snap-fittingly engaged to the leading end of the shroud means and the leading end of the cap is sealingly engaged to the downspout of the valve housing at a location that is in leading relation to the trailing end of the cap.

Significantly, weight members 40 are bushings that cost only about a penny a piece. Where six bushings are provided at the leading end of the bailer and another six, similarly housed, are provided at the trailing end of the bailer, the total cost in weight members is about twelve cents. The weight members of the second incorporated disclosure cost about twenty five cents per piece so the total cost in leading and trailing weight members is about fifty cents per bailer.

It should be observed that a very inexpensive commodity such as sand could be used in lieu of said bushings to lower the cost of the novel bailer even further. The toroidal space between the shroud and the downspout can be filled with loose sand particles and said toroidal space can be closed by the novel aerodynamic cap. Alternatively, an elongate, slim sandbag could be positioned in said toroidal space by wrapping it around the downspout.

Moreover, it is worth noting that an air pocket might exist in the shroud because the bushings or sand bag may not completely fill the shroud. The air pocket would add unwanted buoyancy to the bailer. Accordingly, after the bushings or sand bag are properly positioned, a heavy particulate material such as sand is preferably used to top off the shroud so that no appreciable air bubbles exist therewithin when the cap is snapped or otherwise attached thereto. As an alternate but more expensive buoyancy-reducing means, a one-way vent could be provided in the shroud and air within the shroud could be pumped out.

Figure 9:
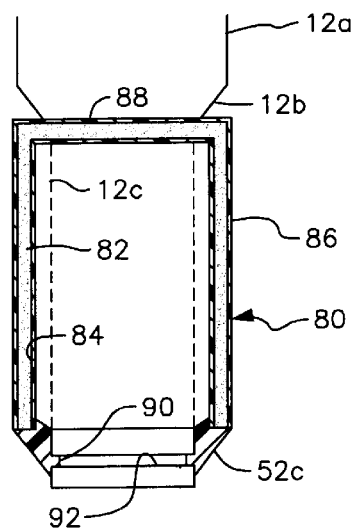
FIG. 9 is a longitudinal sectional view of a weight housing that is snap fit onto the novel valve housing.

FIG. 9 depicts an embodiment that uses sand or other very inexpensive commodity as the sole weight means and which has the advantage of eliminating shroud 42. In this embodiment, a weight housing 80 is snap fit or otherwise attached to valve housing 10. In this way, a bailer manufacturer need not make some bailers with shrouds and some without to meet customer needs. Instead, all bailers may be manufactured with a valve housing 10, and weight housing 80 may be snap fit or attached by other means thereonto when ordered by a customer. Novel weight housing 80 has a main body that defines a toroidal cavity 82 for the retention of loose sand or other weight-providing particulate matter, or for the retention of a bag mean that holds a measured amount of such particulate matter. The toroidal cavity is defined by a cylindrical inner wall 84 that overlies downspout 12c and by a cylindrical outer wall 86 that is concentric with cylindrical inner wall 84 and spaced radially outwardly thereof. An annular trailing wall 88 closes the trailing end of the toroidal cavity and a cap means, 52c, preferably of aerodynamic construction, has a trailing end detachably secured by any suitable means to the leading end of weight housing 80 and a leading end detachably secured by any suitable means to downspout 12c of the bailer. Cap means 52c has a structure similar to that of cap means 52b (FIG. 8), but it could also have a structure like that of cap means 52a (FIG. 7), 52 (FIG. 6) and many other structures. The leading end of weight housing 80 may be secured to downspout 12c by suitable snap fit or other means and the trailing end of weight housing 80 may be secured to frusto-conical walls 12b or cylindrical side walls 12a by suitable snap fit or other attachment means. For example, in FIG. 9 an annular ridge 90 is formed in cap means 52c and said ridge is snap fittingly or otherwise engaged to a mating groove 92 formed in downspout 12c. The longitudinal extent of weight housing 80, in this particular embodiment, is preselected so that the trailing end of weight housing 80 is in abutting relation to frusto-conical walls 12b. A suitable snap fit connection could also be provided at the points of abutment.

Instead of mating grooves and ridges, numerous other snap-fit connections could be employed, including blind bores and mating resilient hooks, bulbous cavities and mating bulbosities and so on. The invention does not reside in the particular attachment means employed, whether of the snap fit type or otherwise, but in the weight housing itself. Although a detachably mounted weight housing is preferred, a weight housing built into the bailer as an integral part thereof is also within the scope of this invention. Such housing would have a detachable cap or nose cone to allow introduction thereinto of a weight means. Moreover, the weight housing is not restricted to a toroidal cavity for the retention of loose particles of sand or sand bags of known weight, or for retention of other loose or packaged materials that provide weight at very low cost. Said cavity could be square or of other predetermined geometrical configuration. A cylindrical weight housing that cooperates with a cylindrical downspout to create a toroidal cavity is believed to represent the optimal cavity due to its aerodynamic aspects and its ease of manufacturing. Moreover, an aerodynamic cap is not required, but is preferred.

It will thus be seen that the objects set forth above, and those made apparent from the foregoing description, are efficiently attained. Since certain changes may be made in the foregoing construction without departing from the scope of the invention, it is intended that all matters contained in the foregoing construction or shown in the accompanying drawings shall be interpreted as illustrative and not in a limiting sense.

It is also to be understood that the following claims are intended to cover all of the generic and specific features of the invention herein described, and all statements of the scope of the invention, which, as a matter of language, might be said to fall therebetween.

Now that the invention has been described,

What is claimed is:

1. A valve assembly for a bailer, comprising:
   a valve housing positioned at a lowermost end of said bailer;
   said valve housing including cylindrical side walls, frusto-conical side walls depending from said cylindrical side walls, and a downspout depending from said frusto-conical side walls;
   a spider that spans a hollow interior of said valve housing at a predetermined position therewithin;
   said spider including a central hub and a plurality of legs that extend radially outwardly from said central hub;
   said spider including an annular ring that interconnects radially outermost ends of said plurality of legs;
   a radially outwardly extending flange formed on said annular ring;

an annular shoulder formed in an interior surface of said cylindrical side walls of said valve housing for supporting said radially outwardly extending flange, said annular shoulder providing a positive positioning means for said spider when said spider is inserted into said valve housing;

said radially outwardly extending flange overlying said shoulder when said spider is operatively positioned within said valve housing;

a flexible and resilient annular ridge formed in said interior surface of said cylindrical side walls of said valve housing in vertically spaced relation to said annular shoulder, said flexible and resilient annular ridge overlying said radially outwardly extending flange when said radially outwardly extending flange is in overlying relation to said annular shoulder;

a central aperture formed in said central hub, said central aperture having an axis of symmetry that is substantially coincident with a longitudinal axis of symmetry of said bailer;

a valve stem slideably received within said central aperture;

a valve body of hemispherical configuration secured to a lowermost end of said valve stem;

a valve seat formed in said frusto-conical side walls;

said valve body being lifted from said valve seat by a predetermined distance as liquid fluid flows into said hollow interior of said bailer, said valve stem and said central aperture of said spider central hub cooperating to maintain said valve body in substantial coincidence with said longitudinal axis of symmetry of said bailer as said valve body rises;

said predetermined distance being determined by said predetermined position of said spider;

said valve stem having a diameter slightly less than a diameter of said central aperture so that said valve stem is maintained in alignment with said longitudinal axis of symmetry of said bailer by said central aperture;

said valve body having a preselected specific gravity that enables said valve body to float on the surface of a preselected liquid fluid collected by said bailer when said valve body is unrestricted;

whereby said valve body returns to said valve seat, when liquid fluid is no longer flowing into said hollow interior of said bailer, by the pressure exerted against a trailing side of said hemispherical valve body by a column of liquid fluid above it;

whereby liquid fluid is admitted into the hollow interior of a bailer as the bailer is lowered into said liquid fluid; and whereby liquid fluid is retained within said hollow interior when said valve body is seated against said valve seat.

2. The valve assembly of claim 1, wherein said trailing side of said valve body is flat.

3. The valve assembly of claim 1, wherein said trailing side of said valve body is concave.

4. The valve assembly of claim 1, wherein said legs have a common extent.

5. The valve assembly of claim 1, wherein the number of legs is four and wherein said legs are equidistantly and circumferentially spaced apart with respect to one another.

6. The valve assembly of claim 1, further comprising a plurality of flutes formed in peripheral walls of said hub that defines said central aperture.

7. A valve assembly for a bailer, comprising:

a valve housing positioned at a lowermost end of said bailer;

said valve housing including cylindrical side walls, frusto-conical side walls depending from said cylindrical side walls, and a downspout depending from said frusto-conical side walls;

a spider that spans a hollow interior of said valve housing at a predetermined position therewithin;

said spider including a central hub and a plurality of legs that extend radially outwardly from said central hub;

said spider including an annular ring that interconnects radially outermost ends of said plurality of legs;

an annular shoulder formed in an interior surface of said cylindrical side walls of said valve housing for supporting said annular ring, said annular shoulder providing a positive positioning means for said spider when said spider is inserted into said valve housing;

said annular ring overlying said shoulder when said spider is operatively positioned within said valve housing;

a flexible and resilient annular ridge formed in said interior surface of said cylindrical side walls of said valve housing in vertically spaced relation to said annular shoulder, said flexible and resilient annular ridge overlying said annular ring when said annular ring is in overlying relation to said annular shoulder;

a central aperture formed in said central hub, said central aperture having an axis of symmetry that is substantially coincident with a longitudinal axis of symmetry of said bailer;

a valve stem slideably received within said central aperture;

a valve body of hemispherical configuration secured to a lowermost end of said valve stem;

a valve seat formed in said frusto-conical side walls;

said valve body being lifted from said valve seat by a predetermined distance as liquid fluid flows into said hollow interior of said bailer, said valve stem and said central aperture of said spider central hub cooperating to maintain said valve body in substantial coincidence with said longitudinal axis of symmetry of said bailer as said valve body rises;

said predetermined distance being determined by said predetermined position of said spider;

said valve stem having a diameter slightly less than a diameter of said central aperture so that said valve stem is maintained in alignment with said longitudinal axis of symmetry of said bailer by said central aperture;

said valve body having a preselected specific gravity that enables said valve body to float on the surface of a preselected liquid fluid collected by said bailer when said valve body is unrestricted;

whereby said valve body returns to said valve seat, when liquid fluid is no longer flowing into said hollow interior of said bailer, by the pressure exerted against a trailing side of said hemispherical valve body by a column of liquid fluid above it;

whereby liquid fluid is admitted into the hollow interior of a bailer as the bailer is lowered into said liquid fluid; and whereby liquid fluid is retained within said hollow interior when said valve body is seated against said valve seat.

8. The valve assembly of claim 7, wherein said trailing side of said valve body is flat.

9. The valve assembly of claim 7, wherein said trailing side of said valve body is concave.

10. The valve assembly of claim 7, wherein said legs have a common extent.

11. The valve assembly of claim 7, wherein the number of legs is four and wherein said legs are equidistantly and circumferentially spaced apart with respect to one another.

12. The valve assembly of claim 7, further comprising a plurality of flutes formed in peripheral walls of said hub that defines said central aperture.

* * * * *